(12) United States Patent
Shalev

(10) Patent No.: US 9,468,517 B2
(45) Date of Patent: Oct. 18, 2016

(54) THERMAL ENERGY APPLICATION FOR PREVENTION AND MANAGEMENT OF ENDOLEAKS IN STENT-GRAFTS

(75) Inventor: Alon Shalev, Ra'anana (IL)

(73) Assignee: ENDOSPAN LTD., Herzilyia Pituach (IL)

(*) Notice: Subject to any disclaimer, the term of this patent is extended or adjusted under 35 U.S.C. 154(b) by 915 days.

(21) Appl. No.: 13/577,161

(22) PCT Filed: Feb. 8, 2011

(86) PCT No.: PCT/IL2011/000135
§ 371 (c)(1),
(2), (4) Date: Oct. 24, 2012

(87) PCT Pub. No.: WO2011/095979
PCT Pub. Date: Aug. 11, 2011

(65) Prior Publication Data
US 2013/0035751 A1    Feb. 7, 2013

Related U.S. Application Data

(60) Provisional application No. 61/302,184, filed on Feb. 8, 2010.

(51) Int. Cl.
*A61F 2/07* (2013.01)
*A61B 5/01* (2006.01)
*A61B 5/00* (2006.01)
(Continued)

(52) U.S. Cl.
CPC . *A61F 2/07* (2013.01); *A61B 5/01* (2013.01); *A61B 5/6862* (2013.01); *A61B 5/026* (2013.01); *A61F 2/89* (2013.01); *A61F 2002/065* (2013.01); *A61F 2002/075* (2013.01); *A61F 2002/077* (2013.01); *A61F 2250/0001* (2013.01)

(58) Field of Classification Search
CPC .............. A61F 2/82; A61F 2/84; A61F 2/07; A61B 19/00
USPC ................................................ 623/1.15–1.38
See application file for complete search history.

(56) References Cited

U.S. PATENT DOCUMENTS

| 4,355,426 A | 10/1982 | MacGregor |
| 4,505,767 A | 3/1985 | Quin |

(Continued)

FOREIGN PATENT DOCUMENTS

| CA | 2 497 704 | 3/2004 |
| EP | 1177780 A2 | 2/2002 |

(Continued)

OTHER PUBLICATIONS

"E-vita® open plus" product brochure (JOTEC GmbH, Hechingen, Germany) (2010).

(Continued)

*Primary Examiner* — Suzette J Gherbi
(74) *Attorney, Agent, or Firm* — Sughrue Mion, PLLC

(57) ABSTRACT

Apparatus (10) is provided, which includes an endovascular stent-graft (20) and a heating device (22) that is coupled to the stent-graft (20). The stent-graft (20) is configured to be implanted in at least one blood vessel in a vicinity of an aneurysm (102). The heating device (22) is configured to apply, to a region (24) external to the stent-graft (20), thermal energy sufficient to coagulate blood flowing into the aneurysm (102). Other embodiments are also described.

43 Claims, 4 Drawing Sheets

(51) Int. Cl.
  *A61B 5/026* (2006.01)
  *A61F 2/06* (2013.01)
  *A61F 2/89* (2013.01)

(56) References Cited

U.S. PATENT DOCUMENTS

| | | |
|---|---|---|
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,234,448 A | 8/1993 | Wholey et al. |
| 5,439,446 A | 8/1995 | Barry |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,824,055 A | 10/1998 | Spiridigliozzi |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,980,552 A | 11/1999 | Pinchasik et al. |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,725 A | 3/2000 | Avellanet |
| 6,059,824 A | 5/2000 | Taheri |
| 6,077,298 A * | 6/2000 | Tu .............................. A61F 2/82 623/1.19 |
| 6,099,497 A | 8/2000 | Adams et al. |
| 6,117,145 A | 9/2000 | Wood et al. |
| 6,156,064 A | 12/2000 | Chouinard |
| 6,168,615 B1 * | 1/2001 | Ken .................. A61B 17/12022 623/1.1 |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,296,661 B1 | 10/2001 | Davila et al. |
| 6,312,458 B1 | 11/2001 | Golds |
| 6,325,823 B1 | 12/2001 | Horzewski et al. |
| 6,344,056 B1 | 2/2002 | Dehdashtian |
| 6,395,018 B1 | 5/2002 | Castaneda |
| 6,428,565 B1 | 8/2002 | Wisselink |
| 6,506,211 B1 | 1/2003 | Skubitz et al. |
| 6,520,988 B1 | 2/2003 | Colombo et al. |
| 6,613,078 B1 | 9/2003 | Barone |
| 6,635,083 B1 | 10/2003 | Cheng et al. |
| 6,652,567 B1 | 11/2003 | Deaton |
| 6,656,214 B1 | 12/2003 | Fogarty et al. |
| 6,692,520 B1 | 2/2004 | Gambale et al. |
| 6,695,833 B1 | 2/2004 | Frantzen |
| 6,743,195 B2 | 6/2004 | Zucker |
| 6,748,953 B2 * | 6/2004 | Sherry ............... A61B 18/1492 128/898 |
| 6,752,826 B2 | 6/2004 | Holloway et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 * | 10/2005 | Ryan ..................... A61B 18/04 606/192 |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski |
| 7,044,962 B2 | 5/2006 | Elliott |
| 7,105,020 B2 | 9/2006 | Greenberg et al. |
| 7,112,217 B2 | 9/2006 | Kugler et al. |
| 7,115,127 B2 | 10/2006 | Lindenbaum et al. |
| 7,144,421 B2 | 12/2006 | Carpenter et al. |
| 7,198,638 B2 | 4/2007 | Dong |
| 7,201,772 B2 | 4/2007 | Schwammenthal |
| 7,223,266 B2 | 5/2007 | Lindenbaum et al. |
| 7,261,733 B1 * | 8/2007 | Brown ................ A61B 5/0028 623/1.34 |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,399,313 B2 * | 7/2008 | Brown ................. A61B 5/0031 623/1.13 |
| 7,407,509 B2 | 8/2008 | Greenberg et al. |
| 7,429,269 B2 | 9/2008 | Schwammenthal |
| 7,442,204 B2 | 10/2008 | Schwammenthal |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,616,997 B2 * | 11/2009 | Kieval ................ A61N 1/0051 607/44 |
| 7,637,939 B2 | 12/2009 | Tischler |
| 7,662,161 B2 | 2/2010 | Briganti et al. |
| 7,662,168 B2 | 2/2010 | McGuckin, Jr. et al. |
| 7,678,141 B2 | 3/2010 | Greenan et al. |
| 7,722,626 B2 | 5/2010 | Middleman et al. |
| 7,731,732 B2 | 6/2010 | Ken |
| 7,803,178 B2 | 9/2010 | Whirley et al. |
| 7,815,673 B2 | 10/2010 | Bloom et al. |
| 7,850,725 B2 | 12/2010 | Vardi |
| 7,887,575 B2 | 2/2011 | Kujawski |
| 7,959,662 B2 | 6/2011 | Erbel et al. |

(56) References Cited

U.S. PATENT DOCUMENTS

| | | | |
|---|---|---|---|
| 7,959,669 B2 | 6/2011 | Chalekian | |
| 8,021,418 B2 | 9/2011 | Gerberding et al. | |
| 8,043,365 B2 | 10/2011 | Thramann | |
| 8,052,741 B2 | 11/2011 | Bruszewski | |
| 8,066,755 B2 | 11/2011 | Zacharias et al. | |
| 8,080,026 B2* | 12/2011 | Konstantino | A61B 17/320725 606/159 |
| 8,080,053 B2 | 12/2011 | Satasiya et al. | |
| 8,100,960 B2 | 1/2012 | Bruszewski | |
| 8,133,267 B2 | 3/2012 | Leonhardt et al. | |
| 8,172,892 B2 | 5/2012 | Chuter et al. | |
| 8,197,475 B2 | 6/2012 | Bruszewski et al. | |
| 8,273,115 B2 | 9/2012 | Hamer | |
| 8,292,885 B2 | 10/2012 | Bruszewski | |
| 8,333,800 B2 | 12/2012 | Bruszewski et al. | |
| 8,506,622 B2 | 8/2013 | Bruszewski et al. | |
| 2001/0000188 A1 | 4/2001 | Lenker et al. | |
| 2001/0004705 A1 | 6/2001 | Killion et al. | |
| 2001/0014823 A1 | 8/2001 | Ressemann et al. | |
| 2001/0034550 A1 | 10/2001 | Buirge et al. | |
| 2001/0044651 A1 | 11/2001 | Steinke et al. | |
| 2001/0044652 A1 | 11/2001 | Moore | |
| 2001/0047198 A1 | 11/2001 | Drasler et al. | |
| 2001/0049550 A1 | 12/2001 | Martin et al. | |
| 2001/0053930 A1 | 12/2001 | Kugler et al. | |
| 2002/0040236 A1 | 4/2002 | Lau et al. | |
| 2002/0099438 A1 | 7/2002 | Furst | |
| 2002/0099441 A1 | 7/2002 | Dehdashtian | |
| 2002/0107564 A1 | 8/2002 | Cox et al. | |
| 2002/0111667 A1 | 8/2002 | Girton | |
| 2002/0123791 A1 | 9/2002 | Harrison | |
| 2002/0156495 A1 | 10/2002 | Brenneman et al. | |
| 2002/0173809 A1 | 11/2002 | Fleischman et al. | |
| 2002/0193864 A1 | 12/2002 | Khosravi et al. | |
| 2003/0040791 A1 | 2/2003 | Oktay | |
| 2003/0074055 A1 | 4/2003 | Haverkost | |
| 2003/0093145 A1 | 5/2003 | Lawrence-Brown et al. | |
| 2003/0125796 A1 | 7/2003 | Dong | |
| 2003/0130720 A1 | 7/2003 | DePalma et al. | |
| 2003/0144725 A1 | 7/2003 | Lombardi | |
| 2003/0153968 A1 | 8/2003 | Geis et al. | |
| 2003/0163187 A1* | 8/2003 | Weber | A61B 18/04 623/1.2 |
| 2003/0191523 A1 | 10/2003 | Hojeibane | |
| 2003/0199967 A1 | 10/2003 | Hartley et al. | |
| 2003/0199968 A1 | 10/2003 | Ainsworth et al. | |
| 2003/0208192 A1 | 11/2003 | Truckai et al. | |
| 2003/0212449 A1 | 11/2003 | Cox | |
| 2003/0236567 A1 | 12/2003 | Elliot | |
| 2004/0015227 A1 | 1/2004 | Vardi et al. | |
| 2004/0015229 A1 | 1/2004 | Fulkerson et al. | |
| 2004/0098091 A1 | 5/2004 | Erbel et al. | |
| 2004/0106972 A1 | 6/2004 | Deaton | |
| 2004/0106978 A1 | 6/2004 | Greenberg et al. | |
| 2004/0117003 A1 | 6/2004 | Ouriel et al. | |
| 2004/0133266 A1 | 7/2004 | Clerc et al. | |
| 2004/0162606 A1 | 8/2004 | Thompson | |
| 2004/0171978 A1 | 9/2004 | Shalaby | |
| 2004/0181149 A1 | 9/2004 | Langlotz et al. | |
| 2004/0215327 A1 | 10/2004 | Doig et al. | |
| 2005/0033406 A1 | 2/2005 | Barnhart et al. | |
| 2005/0049678 A1 | 3/2005 | Cocks et al. | |
| 2005/0065545 A1 | 3/2005 | Wallace | |
| 2005/0085900 A1 | 4/2005 | Case et al. | |
| 2005/0102018 A1 | 5/2005 | Carpenter et al. | |
| 2005/0102021 A1 | 5/2005 | Osborne | |
| 2005/0131517 A1 | 6/2005 | Hartley et al. | |
| 2005/0143802 A1* | 6/2005 | Soykan | A61F 2/02 623/1.11 |
| 2005/0149166 A1 | 7/2005 | Schaeffer et al. | |
| 2005/0154448 A1 | 7/2005 | Cully et al. | |
| 2005/0171598 A1 | 8/2005 | Schaeffer | |
| 2005/0203606 A1 | 9/2005 | VanCamp | |
| 2005/0222649 A1* | 10/2005 | Capuano | A61B 18/02 607/88 |
| 2005/0222667 A1 | 10/2005 | Hunt | |
| 2005/0222668 A1 | 10/2005 | Schaeffer et al. | |
| 2005/0222669 A1 | 10/2005 | Purdy | |
| 2005/0266042 A1 | 12/2005 | Tseng | |
| 2005/0283188 A1 | 12/2005 | Loshakove et al. | |
| 2006/0015170 A1 | 1/2006 | Jones et al. | |
| 2006/0030911 A1 | 2/2006 | Letort | |
| 2006/0052799 A1 | 3/2006 | Middleman et al. | |
| 2006/0069426 A1 | 3/2006 | Weinberger | |
| 2006/0095104 A1* | 5/2006 | Magers | A61F 7/12 607/105 |
| 2006/0100684 A1 | 5/2006 | Elliott | |
| 2006/0106406 A1 | 5/2006 | Weinberger | |
| 2006/0149360 A1 | 7/2006 | Schwammenthal | |
| 2006/0155358 A1 | 7/2006 | LaDuca et al. | |
| 2006/0155366 A1 | 7/2006 | LaDuca et al. | |
| 2006/0167476 A1 | 7/2006 | Burdulis, Jr. et al. | |
| 2006/0173530 A1 | 8/2006 | Das | |
| 2006/0190070 A1 | 8/2006 | Dieck et al. | |
| 2006/0193892 A1 | 8/2006 | Furst et al. | |
| 2006/0212113 A1 | 9/2006 | Shaolian et al. | |
| 2006/0229709 A1 | 10/2006 | Morris et al. | |
| 2006/0241740 A1 | 10/2006 | Vardi et al. | |
| 2006/0271166 A1 | 11/2006 | Thill et al. | |
| 2006/0281966 A1 | 12/2006 | Peacock, III | |
| 2007/0016281 A1 | 1/2007 | Melsheimer | |
| 2007/0021822 A1 | 1/2007 | Boatman | |
| 2007/0043425 A1 | 2/2007 | Hartley et al. | |
| 2007/0050011 A1 | 3/2007 | Klein et al. | |
| 2007/0055326 A1 | 3/2007 | Farley et al. | |
| 2007/0055350 A1 | 3/2007 | Erickson et al. | |
| 2007/0055358 A1 | 3/2007 | Krolik et al. | |
| 2007/0060989 A1 | 3/2007 | Deem et al. | |
| 2007/0061002 A1 | 3/2007 | Paul, Jr. et al. | |
| 2007/0073373 A1 | 3/2007 | Bonsignore | |
| 2007/0088425 A1 | 4/2007 | Schaeffer | |
| 2007/0112344 A1 | 5/2007 | Keilman | |
| 2007/0135677 A1 | 6/2007 | Miller et al. | |
| 2007/0142896 A1 | 6/2007 | Anderson et al. | |
| 2007/0150051 A1 | 6/2007 | Arnault De La Menardiere et al. | |
| 2007/0156167 A1 | 7/2007 | Connors et al. | |
| 2007/0167898 A1 | 7/2007 | Peters et al. | |
| 2007/0167955 A1 | 7/2007 | Arnault De La Menardiere et al. | |
| 2007/0168018 A1 | 7/2007 | Amplatz et al. | |
| 2007/0179598 A1 | 8/2007 | Duerig | |
| 2007/0185565 A1 | 8/2007 | Schwammenthal et al. | |
| 2007/0207186 A1 | 9/2007 | Scanlon et al. | |
| 2007/0208410 A1 | 9/2007 | Berra et al. | |
| 2007/0213805 A1 | 9/2007 | Schaeffer et al. | |
| 2007/0213807 A1 | 9/2007 | Roubin et al. | |
| 2007/0219610 A1 | 9/2007 | Israel | |
| 2007/0219627 A1 | 9/2007 | Chu et al. | |
| 2007/0233229 A1 | 10/2007 | Berra et al. | |
| 2007/0237973 A1 | 10/2007 | Purdy et al. | |
| 2007/0239256 A1* | 10/2007 | Weber | A61B 5/055 623/1.15 |
| 2007/0244542 A1 | 10/2007 | Greenan et al. | |
| 2007/0244543 A1 | 10/2007 | Mitchell | |
| 2007/0244547 A1 | 10/2007 | Greenan | |
| 2007/0250154 A1 | 10/2007 | Greenberg et al. | |
| 2007/0255388 A1 | 11/2007 | Rudakov et al. | |
| 2008/0002871 A1 | 1/2008 | Gunzert-Marx et al. | |
| 2008/0015673 A1 | 1/2008 | Chuter | |
| 2008/0033527 A1* | 2/2008 | Nunez | A61B 5/0215 623/1.13 |
| 2008/0058918 A1 | 3/2008 | Watson | |
| 2008/0064957 A1* | 3/2008 | Spence | A61M 25/1002 600/439 |
| 2008/0109066 A1 | 5/2008 | Quinn | |
| 2008/0114445 A1 | 5/2008 | Melsheimer et al. | |
| 2008/0147173 A1 | 6/2008 | McIff et al. | |
| 2008/0167704 A1 | 7/2008 | Wright et al. | |
| 2008/0176271 A1* | 7/2008 | Silver | A61B 5/0031 435/29 |
| 2008/0195190 A1 | 8/2008 | Bland et al. | |
| 2008/0195191 A1 | 8/2008 | Luo et al. | |
| 2008/0215134 A1 | 9/2008 | Lawrence-Brown | |
| 2008/0249598 A1 | 10/2008 | Sherry | |
| 2008/0269789 A1 | 10/2008 | Eli | |

(56) References Cited

U.S. PATENT DOCUMENTS

| | | |
|---|---|---|
| 2008/0275540 A1 | 11/2008 | Wen |
| 2008/0275542 A1 | 11/2008 | LaDuca et al. |
| 2008/0288044 A1 | 11/2008 | Osborne |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069882 A1 | 3/2009 | Venturelli et al. |
| 2009/0082841 A1 | 3/2009 | Zacharias et al. |
| 2009/0099648 A1 | 4/2009 | Yu |
| 2009/0099649 A1 | 4/2009 | Chobotov et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev |
| 2010/0070019 A1 | 3/2010 | Shalev |
| 2010/0082091 A1 | 4/2010 | Berez et al. |
| 2010/0161026 A1 | 6/2010 | Brocker et al. |
| 2010/0211159 A1 | 8/2010 | Schmid et al. |
| 2010/0256725 A1 | 10/2010 | Rasmussen |
| 2010/0274345 A1* | 10/2010 | Rust .......................... A61F 2/07 623/1.13 |
| 2010/0292774 A1 | 11/2010 | Shalev |
| 2010/0318171 A1 | 12/2010 | Porter et al. |
| 2011/0022149 A1* | 1/2011 | Cox ................ A61B 17/12172 623/1.11 |
| 2011/0093002 A1 | 4/2011 | Rucker et al. |
| 2011/0125251 A1 | 5/2011 | Cottone et al. |
| 2011/0208289 A1 | 8/2011 | Shalev |
| 2011/0208296 A1 | 8/2011 | Duffy et al. |
| 2011/0208297 A1 | 8/2011 | Tuval |
| 2011/0208298 A1 | 8/2011 | Tuval |
| 2011/0218607 A1 | 9/2011 | Arbefeuille et al. |
| 2011/0257725 A1* | 10/2011 | Argentine ................ A61F 2/07 623/1.15 |
| 2011/0262684 A1* | 10/2011 | Wintsch .................... A61F 2/07 428/99 |
| 2011/0264184 A1 | 10/2011 | Heltai |
| 2011/0288622 A1 | 11/2011 | Chan et al. |
| 2012/0143317 A1* | 6/2012 | Cam ................ A61B 17/12118 623/1.35 |
| 2012/0158038 A1* | 6/2012 | Leschinsky .......... A61B 5/6876 606/200 |
| 2013/0274866 A1* | 10/2013 | Cox ................ A61B 17/12172 623/1.18 |
| 2014/0364930 A1* | 12/2014 | Strauss ............ A61B 17/12118 623/1.11 |

FOREIGN PATENT DOCUMENTS

| | | |
|---|---|---|
| EP | 1325716 A1 | 7/2003 |
| JP | 2000-279533 A | 10/2000 |
| JP | 2002-253682 | 9/2002 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 2006/070372 | 7/2006 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/045238 | 4/2010 |
| WO | 2010/062355 | 6/2010 |
| WO | 2010/088776 | 8/2010 |
| WO | 2010-128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |
| WO | 2012/049679 | 4/2012 |
| WO | 2012/104842 | 8/2012 |
| WO | 2012/111006 | 8/2012 |
| WO | 2012/117395 | 9/2012 |

OTHER PUBLICATIONS

An English Translation of an Office Action dated Aug. 25, 2011, which issued during the prosecution of Chinese Patent Application No. 200880014919.9.

Fonseca A et al., "Intravascular ultrasound assessment of the novel AngioSculpt scoring balloon catheter for the treatment of complex coronary lesions," J Invasive Cardiol 20(1):21-7 (Jan. 2008).

An International Search Report and a Written Opinion both dated Sep. 24, 2012, which issued during the prosecution of Applicant's PCT/IL2012/000060.

Khlif H et al., "Contribution to the Improvement of Textile Vascular Prostheses Crimping," Trends in Applied Sciences Research 6(9):1019-1027 (2011).

An International Search Report and a Written Opinion both dated Jul. 13, 2012, which issued during the prosecution of Applicant's PCT/IL2012/000083.

An International Search Report and a Written Opinion both dated Jul. 17, 2012, which issued during the prosecution of Applicant's PCT/IL2012/000095.

An International Search Report and a Written Opinion both dated Aug. 31, 2012, which issued during the prosecution of Applicant's PCT/IL2012/000148.

An International Search Report and a Written Opinion both dated Sep. 6, 2012, which issued during the prosecution of Applicant's PCT/IL2012/000190.

An International Search Report and a Written Opinion both dated Jun. 19, 2012, which issued during the prosecution of Applicant's PCT/IL2012/000241.

An International Search Report and a Written Opinion both dated Nov. 27, 2012, which issued during the prosecution of Applicant's PCT/IL2012/000300.

An International Search Report and a Written Opinion both dated Feb. 4, 2011, which issued during the prosecution of Applicant's PCT/IB2010/052861.

An International Search Report and a Written Opinion both dated Sep. 29, 2008, which issued during the prosecution of Applicant's PCT/IL08/000287.

(56) References Cited

OTHER PUBLICATIONS

An International Search Report and a Written Opinion both dated Mar. 11, 2009, which issued during the prosecution of Applicant's PCT/IL2007/001312.
An International Search Report and a Written Opinion both dated Jun. 30, 2009, which issued during the prosecution of Applicant's PCT/IL2008/001621.
An International Search Report and a Written Opinion both dated Nov. 5, 2010, which issued during the prosecution of Applicant's PCTIL2010000549.
An International Search Report and a Written Opinion both dated Dec. 3, 2010, which issued during the prosecution of Applicant's PCT/IL2010/000564.
An International Search Report and a Written Opinion both dated Mar. 10, 2011, which issued during the prosecution of Applicant's PCT/IL2010/000917.
An International Search Report and a Written Opinion both dated Aug. 4, 2011, which issued during the prosecution of Applicant's PCT/IL2010/000999.
An International Search Report and a Written Opinion both dated Mar. 30, 2011, which issued during the prosecution of Applicant's PCT/IL2010/001018.
An International Search Report and a Written Opinion both dated Apr. 18, 2011, which issued during the prosecution of Applicant's PCT/IL2010/001037.
An International Search Report and a Written Opinion both dated May 23, 2011, which issued during the prosecution of Applicant's PCT/IL2010/001087.
An International Search Report and a Written Opinion both dated Jun. 28, 2011, which issued during the prosecution of Applicant's PCT/IL2011/000135.
An International Search Report dated Oct. 4, 2012, which issued during the prosecution of Applicant's PCT/IL2012/000269.
An Office Action dated Apr. 27, 2011, which issued during the prosecution of U.S. Appl. No. 12/447,684.
An Office Action dated Nov. 12, 2010, which issued during the prosecution of U.S. Appl. No. 12/447,684.
An Office Action dated Mar. 24, 2011, which issued during the prosecution of U.S. Appl. No. 12/529,936.
An Office Action dated Oct. 28, 2011, which issued during the prosecution of U.S. Appl. No. 12/529,936.
An Office Action dated Jun. 19, 2012, which issued during the prosecution of U.S. Appl. No. 12/808,037.
An Office Action dated Oct. 11, 2012, which issued during the prosecution of U.S. Appl. No. 13/031,871.
An International Search Report and a Written Opinion both dated Nov. 26, 2013, which issued during the prosecution of Applicant's PCT/IL13/50656.
An Office Action dated Dec. 2, 2013, which issued during the prosecution of U.S. Appl. No. 13/807,880.
An International Search Report and a Written Opinion both dated Mar. 15, 2013, which issued during the prosecution of Applicant's PCT/IL2012/050424.
An Office Action dated May 20, 2013, which issued during the prosecution of U.S. Appl. No. 13/807,880.
An International Search Report and Written Opinion issued in PCT/IL2012/050506, dated Jun. 14, 2013.
European search report issued in Appl. No. 11739497.3, dated Mar. 11, 2016.
European search report issued in Appl. No. 13825456.0, dated Mar. 15, 2016.

* cited by examiner

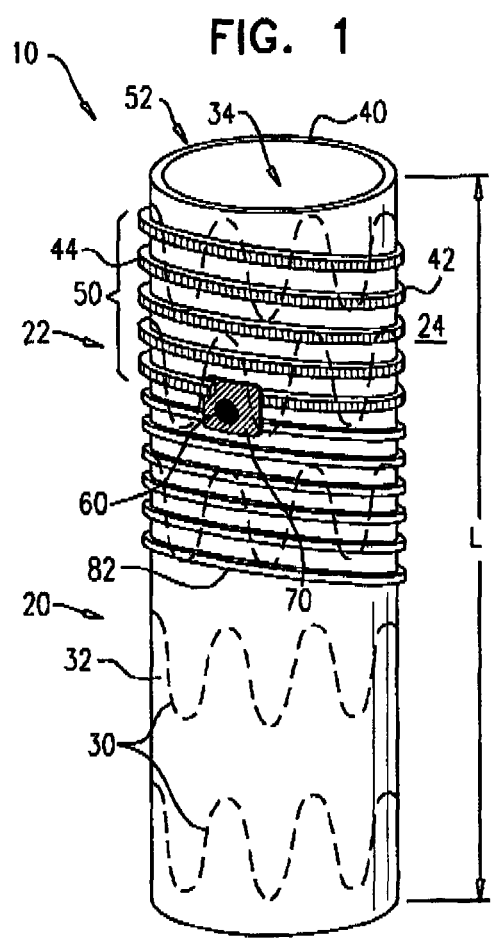
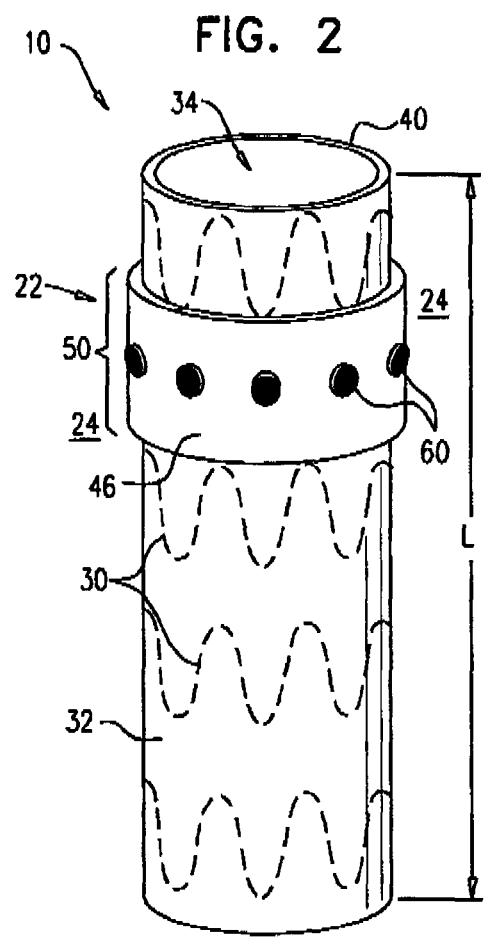

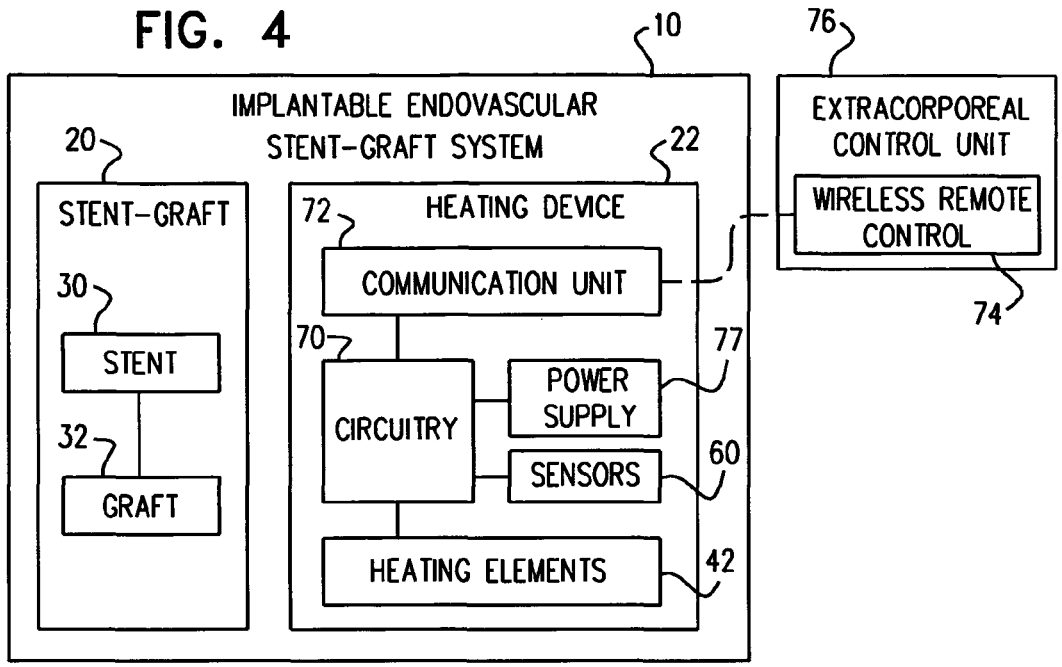
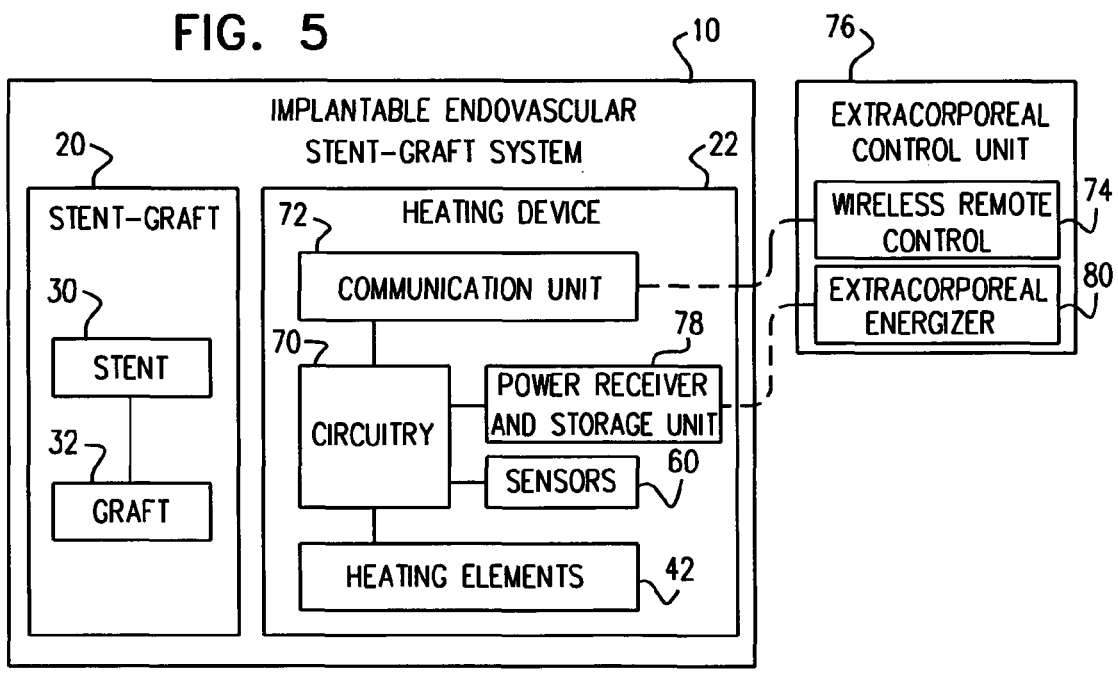

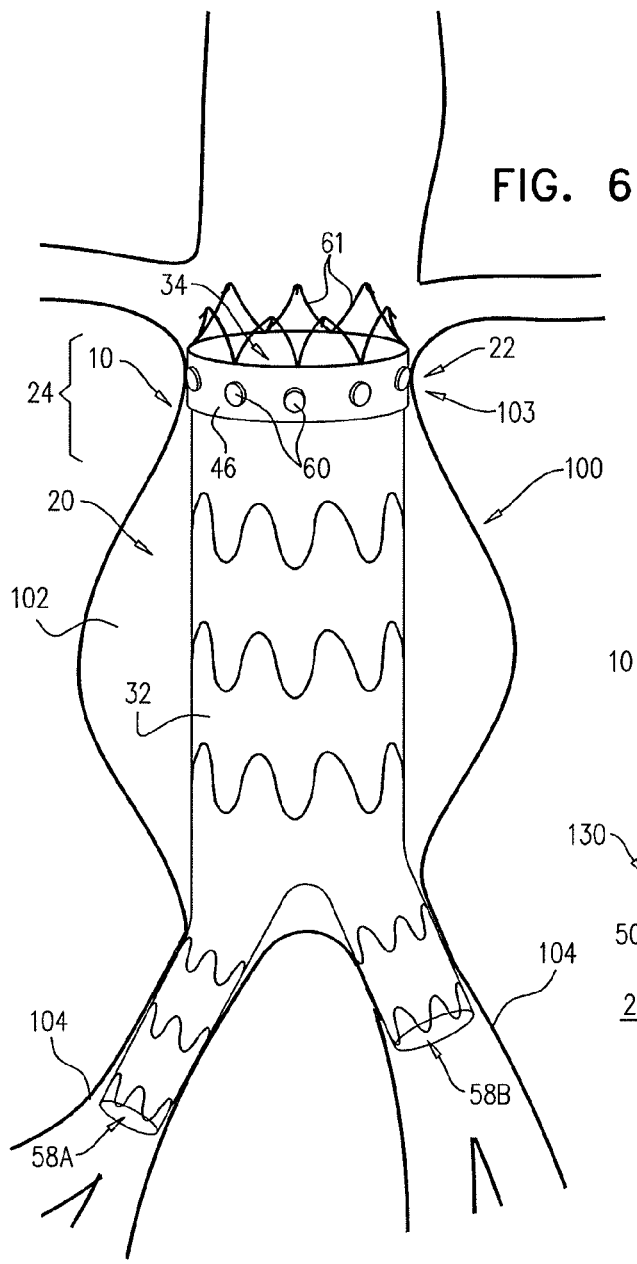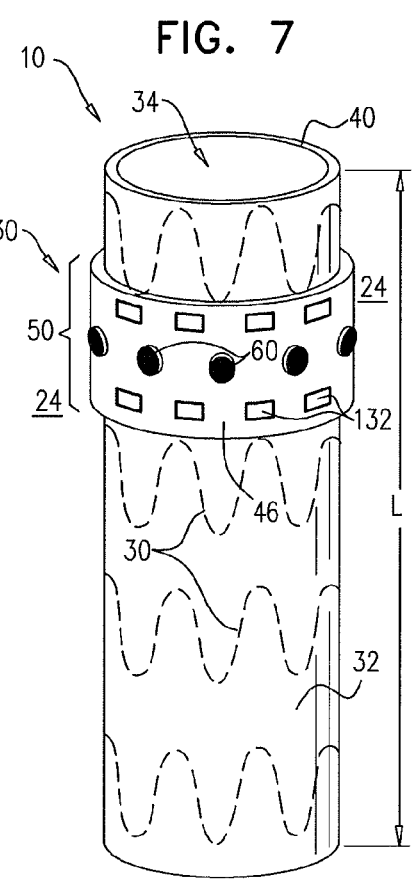

THERMAL ENERGY APPLICATION FOR PREVENTION AND MANAGEMENT OF ENDOLEAKS IN STENT-GRAFTS

CROSS REFERENCE TO RELATED APPLICATIONS

This application is a National Stage of International Application No. PCT/IL2011/000135 filed Feb. 8, 2011, claiming priority based on U.S. Provisional Patent Application No. 61/302,184, filed Feb. 8, 2011, the contents of all of which are incorporated herein by reference in their entirety.

FIELD OF THE APPLICATION

This present application relates generally to prostheses and treatment methods, and specifically to tubular prostheses, including endovascular grafts and stent-grafts, and treatment techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms.

"Endoleak" is the persistent flow of blood into the aneurismal sac after implantation of an endovascular prosthesis. The management of some types of endoleak remains controversial, although most can be successfully occluded with surgery, further stent implantation, or embolization. Four types of endoleaks have been defined, based upon their proposed etiology, as described below.

A type I endoleak, which occurs in up to 10 percent of endovascular aortic aneurysm repairs, is due to an incompetent seal at either the proximal or distal attachment sites of the vascular prosthesis, resulting in blood flow at the end of the prosthesis into the aneurismal sac. Etiologies include undersizing of the diameter of the endograft at the attachment site and ineffective attachment to a vessel wall that is heavily calcified or surrounded by thick thrombus. Type I failures have also been found to be caused by a continual expansion of the aneurysm neck (the portion of the aorta extending cephalad or caudad from the aneurysm, and is not dilated). This expansion rate has been estimated to be about one millimeter per year. Because the aneurysm neck expands beyond the natural resting diameter of the prosthesis, one or more passageways are defined about the prosthesis in communication with the aneurismal sac. Additionally, Type I endoleaks may be caused when circular prostheses are implanted in non-circular aortic lumens, which may be caused by irregular vessel formation and/or calcified topography of the lumen of the aorta.

Type I endoleaks may occur immediately after placement of the prosthesis, or may be delayed. A delayed type I endoleak may be seen during follow-up studies if the prosthesis is deployed into a diseased segment of aorta that dilates over time, leading to a breach in the seal at the attachment site.

Type I endoleaks must be repaired as soon as they are discovered, because the aneurismal sac remains exposed to systemic pressure, predisposing to aneurysmal rupture, and spontaneous closure of the leak is rare. If discovered at the time of initial placement, repair may consist of reversal of anticoagulation and reinflation of the deployment balloon for an extended period of time. These leaks may also be repaired with small extension grafts that are placed over the affected end. These methods are usually sufficient to exclude the aneurysm. Conversion to an open surgical repair may be needed in the rare situation in which the leak is refractory to percutaneous treatment.

Type II endoleaks are the most prevalent type, occurring in 10 to 25 percent of endovascular aortic aneurysm repairs, and are characterized by flow into and out of the aneurismal sac from patent branch vessels. These endoleaks are most often identified on the post procedural CT, in which these leaks appear as collections of contrast outside of the endograft, but within the aneurismal sac. The most frequent sources of type II endoleaks are collateral backflow through patent lumbar arteries and a patent inferior mesenteric artery. Because the sac fills through a collateral network, the endoleak may not be visualized on the arterial phase of CT scanning; delayed imaging is thus required.

Type III and type IV endoleaks are much less common. Type III endoleaks represent flow into the aneurismal sac from separation between components of a modular system, or tears in the endograft fabric. Type IV endoleaks are due to egress of blood through the pores in the fabric. Type IV leaks heal spontaneously, while type III leaks are repaired with an additional endograft to eliminate systemic flow and pressure in the aneurysm.

As can be readily appreciated, even with the successful implantation of an endovascular prosthesis, failures may occur thereafter. It has been found that type I failures may affect up to 5-10% of all implanted prostheses. Accordingly, there is a clear need for an endovascular prosthesis which can reduce the likelihood of, and ideally eliminate, type I failures.

PCT Publication WO 2008/107885 to Shalev et al., and US Patent Application Publication 2010/0063575 to Shalev et al. in the US national stage thereof, which are incorporated herein by reference, describe a multiple-component expandable endoluminal system for treating a lesion at a bifurcation, including a self expandable tubular root member having a side-looking engagement aperture, and a self expandable tubular trunk member comprising a substantially blood impervious polymeric liner secured therealong. Both have a radially-compressed state adapted for percutaneous intraluminal delivery and a radially-expanded state adapted for endoluminal support.

The following references may be of interest:

U.S. Pat. No. 4,938,740

U.S. Pat. No. 5,824,040 to Cox et al.

U.S. Pat. No. 7,044,962 to Elliott

US Patent Application Publication 2006/0229709 to Morris et al.

US Patent Application Publication 2006/0241740 to Vardi et al.

US Patent Application Publication 2008/0109066 to Quinn

SUMMARY OF APPLICATIONS

In some applications of the present invention, an endovascular stent-graft system is provided for implantation in at least one blood vessel of a patient in a vicinity of an aneurysm. The endovascular stent-graft system comprises an endovascular stent-graft and a heating device, which is coupled to the stent-graft. The heating device is configured to apply, to a region external to the stent-graft, thermal energy sufficient to coagulate blood flowing into the aneurysm. For some applications, the heating device is activated in response to ascertaining that the patient is at risk of suffering from a type I endoleak, and application of the thermal energy reduces or prevents the type I endoleak. Alternatively, the heating device is activated in response to ascertaining that the patient suffers from a type I endoleak, and application of the thermal energy treats the type I endoleak. Thus the application of the thermal energy may be prophylactic, therapeutic, or both. The thermal energy may be applied exactly one time, periodically, or based on an assessment of the patient's condition.

For some applications, the heating device comprises one or more heating elements that are coupled to the stent-graft, such as at least one heating coil, which may be wrapped around a portion of the stent-graft. For some applications, the heating device comprises circuitry and one or more sensors, such as one or more temperature sensors, and/or one or more blood flow sensors. For some applications, the circuitry is configured to monitor at least one temperature and/or at least one parameter of blood flow, and to drive the one or more heating elements to apply the thermal energy responsively to the at least one monitored temperature and/or blood flow parameter.

For some applications, the heating device is configured for wireless control from an extracorporeal location. For some of these applications, the heating device comprises a communication unit, which is configured to communicate with a wireless remote control unit of an extracorporeal control unit. For some applications, the heating device further comprises a power supply. Alternatively or additionally, for some applications, the heating device further comprises a power receiver and storage unit, which is configured to wirelessly receive energy from an extracorporeal energizer.

For some applications, the stent-graft system comprises a current application device, rather than the heating device. The current application device typically comprises a plurality of electrodes, and the circuitry is configured to drive the electrodes to apply, to the region external to the stent-graft, an electrical current sufficient to coagulate blood flowing into the aneurysm.

There is therefore provided, in accordance with an application of the present invention, apparatus including:

an endovascular stent-graft, configured to be implanted in at least one blood vessel in a vicinity of an aneurysm; and a heating device, which is coupled to the stent-graft, and which is configured to apply, to a region external to the stent-graft, thermal energy sufficient to coagulate blood flowing into the aneurysm.

For some applications, the heating device is configured to set a level of the thermal energy to be insufficient to cause tissue ablation of an adventitial layer of the aneurysm. For some applications, the heating device is configured to set a level of the thermal energy to increase an average temperature in the region by between 3 and 7 degrees C. For some applications, the heating device is configured to set a level of the thermal energy to increase an average temperature in the region by no more than 6 degrees C. For some applications, the heating device is configured to set a level of the thermal energy to increase an average temperature in the region to between a minimum and a maximum temperature, the minimum temperature between 39 and 41 degrees C., and the maximum temperature between 41 and 45 degrees C. For some applications, the stent-graft is shaped so as to define a lumen when in a radially-expanded state, and the heating device is configured to increase an average temperature within the lumen by no more than 2 degrees C.

For some applications, the region surrounds at least 180 degrees of a circumference of the stent-graft, such as 360 degrees of the circumference, and the heating device is configured to apply the thermal energy to the region.

For some applications, the stent-graft is shaped so as to define a lumen when in a radially-expanded state, and the heating, device includes one or more heating elements that span at least 300 degrees of a circumference of the lumen, such as 360 degrees of the circumference, at one or more locations selected from the group consisting of: one or more locations outside of the lumen, and one or more locations within the lumen.

For some applications, the stent-graft and the heating device are configured to be entirely implanted in the at least one blood vessel, such that no portion of either of the stent-graft or the heating device extends outside of the at least one blood vessel.

For some applications, the heating device includes one or more heating elements, which include at least one heating coil. For some applications, the heating coil is wrapped around a portion of the stent-graft. For some applications, the heating coil is wrapped around a complete circumference of the stent-graft at least once. For some applications, the apparatus further includes an extracorporeal control unit, which is configured to wirelessly transmit energy to the heating coil. For some applications, the extracorporeal control unit is configured to inductively drive current through the heating coil to generate the thermal heat.

For some applications, the stent-graft is shaped so as to define a lumen when in a radially-expanded state, the heating device includes one or more heating elements having respective surfaces that apply the thermal energy, the heating elements that collectively are positioned along a longitudinal portion of the lumen, and a combined total area of the surfaces is between 1% and 10% of an average cross-sectional area of the lumen along the longitudinal portion.

For some applications, the heating device includes one or more heating elements and circuitry configured to drive the heating elements to apply the thermal energy. For some applications, the circuitry is configured to drive the one or more heating elements to apply the thermal energy such that an average energy consumption rate over all five-second periods of heating does not exceed 5 W.

For some applications, the circuitry is configured to drive the heating elements to apply the thermal energy generally continuously. For some applications, the circuitry is configured to drive the heating elements to apply the thermal energy periodically. For some applications, the circuitry is configured to drive the heating elements to apply the thermal energy intermittently.

For some applications, the heating device is configured to apply the thermal energy such that an average energy consumption rate over all five-second periods of heating does not exceed 5 W.

For some applications, the stent-graft is shaped so as to define a lumen having an axial length when in a radially-expanded state, and the heating device includes one or more heating elements that collectively are positioned along no more than 20% of the axial length.

For some applications, the stent-graft, when in a radially-expanded state, is shaped so as to define a lumen having an upstream end, and the heating device includes one or more heating elements that are coupled to the stent-graft in a vicinity of the upstream end. For some applications, the lumen is a main lumen, and the stent-graft is shaped so as to define a bifurcated downstream end, which defines first and second generally tubular downstream lumens that are in fluid communication with the main lumen. For some applications, the upstream end is flared.

For some applications, the heating device is configured for wireless control from an extracorporeal location. For some applications, the apparatus further includes an extracorporeal control unit, which is configured to wirelessly control the heating device. For some applications, the heating device includes a wireless receiver, and the apparatus further includes an extracorporeal control unit, configured to wirelessly transmit energy to the wireless receiver.

For any of the applications described above; the heating device may include at least one sensor, and one or more heating elements. For some applications, the sensor includes a temperature sensor, and the heating device further includes circuitry which is configured to monitor at least one temperature using the temperature sensor, and to drive the one or more heating elements to apply the thermal energy responsively to the at least one monitored temperature. For some applications, the stent-graft is shaped so as to define at least one lumen when in a radially-expanded state, and the at least one temperature is selected from the group consisting of: a temperature of blood flowing within the lumen, and a temperature of blood external to the lumen. For some applications, the circuitry is configured to maintain the temperature of the blood external to the lumen at between a minimum and a maximum temperature, the minimum temperature between 39 and 41 degrees C., and the maximum temperature between 41 and 45 degrees C. For some applications, the circuitry is configured to set at least one heating parameter responsively to the at least one temperature, so as to selectively coagulate the blood flowing into the aneurysm without causing substantial coagulation of the blood flowing within the lumen.

For some applications, the sensor includes a blood flow sensor, and the heating device further includes circuitry which is configured to monitor at least one blood flow parameter using the blood flow sensor, and to drive the one or more heating elements to apply the thermal energy responsively to the at least one monitored blood flow parameter. For some applications, the stent-graft is shaped so as to define at least one lumen when in a radially-expanded state, and the at least one blood flow parameter is selected from the group consisting of: a blood flow parameter of blood flowing within the lumen, and a blood flow parameter of blood external to the lumen. For some applications, the circuitry is configured to set at least one heating parameter responsively to the at least one monitored blood flow parameter, so as to selectively coagulate the blood flowing into the aneurysm without causing substantial coagulation of the blood flowing within the lumen.

For some applications, the stent-graft is shaped so as to define a lumen when in a radially-expanded state, and the at least one sensor is coupled to an external surface of the lumen. Alternatively or additionally, for some applications, the stent-graft is shaped so as to define a lumen when in a radially-expanded state, and the at least one sensor is positioned within the lumen.

For some applications, the stent-graft, when in a radially-expanded state, is shaped so as to define a lumen having an upstream end, and the at least one sensor is positioned in a vicinity of the upstream end.

For some applications, the at least one sensor includes a temperature sensor. Alternatively or additionally, for some applications, the at least one sensor includes a blood flow sensor.

For some applications, the at least one sensor includes at least four sensors, distributed around a circumference of the stent-graft.

For any of the applications described above, the stent-graft may include a stent and a graft coupled to the stent, which stent and graft are generally tubular when the stent-graft is in an radially-expanded state. For some applications, the stent includes a plurality of structural stent elements, and the heating device drives an electrical current through a portion of the structural stent elements in order to apply the thermal energy. For some applications, the stent includes a self-expanding elastic material.

For some applications, the graft includes a polymer, which, for example, may be selected from the group consisting of: a fluoropolymer, polytetrafluoroethylene, a polyester, and polyethylene therephthalate.

For some applications, the stent is formed from tubing.

For some applications, the stent includes a superelastic alloy. For some applications, the stent includes a material selected the group consisting of: stainless steel, a cobalt chromium alloy, a platinum/tungsten alloy, and a nickel-titanium alloy.

For some applications, the stent includes a wire stent. For some applications, the stent includes a ribbon stent.

For any of the applications described above, the stent-graft may be shaped so as to define at least one flared end.

For any of the applications described above, the stent-graft and the heating device may be configured to assume respective radially-compressed states for transvascular delivery to the at least one blood vessel, and to transition to respective radially-expanded states upon deployment in the at least one blood vessel. For some applications, the apparatus further includes a delivery catheter, in which the stent-graft and the heating device are initially positioned in their respective radially-compressed states.

For any of the applications described above, the heating device may be configured with one or more electrical parameters that are set to coagulate the blood flowing into the aneurysm, the parameters selected from the group consisting of: timing of the application of, the thermal energy, and amplitude of the thermal energy.

There is further provided, in accordance with an application of the present invention, a method including:

identifying that a patient has an aneurysm; and in response to the identifying, activating an implanted heating device to apply, to a region external to an endovascular stent-graft implanted in at least one blood vessel of the patient, which region is upstream of the aneurysm, thermal energy sufficient to coagulate blood flowing into the aneurysm.

For some applications, identifying includes ascertaining that the patient is at risk of suffering from a type I endoleak, and activating includes activating the heating device to apply the thermal energy to coagulate the blood so as to reduce or prevent the type I endoleak. Alternatively or additionally, for some applications, identifying includes ascertaining that the patient suffers from a type I endoleak, and activating includes activating the heating device to apply the thermal energy to coagulate the blood so as to treat the type I endoleak.

There is still further provided, in accordance with an application of the present invention, a method including:

implanting, in at least one blood vessel of a patient in a vicinity of an aneurysm, an endovascular stent-graft and a heating device coupled thereto; and activating the heating device to apply, to a region external to the stent-graft and upstream of the aneurysm, thermal energy sufficient to coagulate blood flowing into the aneurysm.

For some applications, activating includes ascertaining that the patient has is at risk of suffering from a type I endoleak, and activating the heating device to apply the thermal energy to coagulate the blood so as to reduce or prevent the type I endoleak. Alternatively or additionally, for some applications, activating includes ascertaining that the patient suffers from a type I endoleak, and activating the heating device to apply the thermal energy to coagulate the blood so as to treat the type I endoleak.

For some applications, implanting includes implanting the stent-graft and the heating device in an artery.

For some applications, implanting includes implanting the stent-graft and the heating device entirely within the at least one blood vessel, such that no portion of either of the stent-graft or the heating device extends outside of the at least one blood vessel.

For some applications, implanting includes transvascularly introducing the stent-graft and the heating device into the at least one blood vessel. For some applications, transvascularly introducing includes transvascularly introducing the stent-graft and the heating device while the stent-graft and the heating device are positioned in a delivery catheter in respective radially-compressed states, and deploying the stent-graft and the heating device from the delivery catheter in the at least one blood vessel, so that the stent-graft and the heating element assume respective radially-expanded states.

For some applications, the stent-graft is shaped so as to define at least one lumen when in a radially-expanded state, and activating includes activating the heating device to apply the thermal energy at a level that selectively coagulates the blood flowing into the aneurysm without causing substantial coagulation of blood flowing within the lumen.

For some applications, activating includes activating the heating device to set a level of the thermal energy to be insufficient to cause tissue ablation of an adventitial layer of the aneurysm. For some applications, activating includes activating the heating device to set a level of the thermal energy to increase an average temperature in the region by between 3 and 7 degrees C. For some applications, activating includes activating the heating device to set a level of the thermal energy to increase an average temperature in the region by no more than 6 degrees C. For some applications, activating includes activating the heating device to set a level of the thermal energy to increase an average temperature in the region to between a minimum and a maximum temperature, the minimum temperature between 39 and 41 degrees C., and the maximum temperature between 41 and 45 degrees C. For some applications, the stent-graft is shaped so as to define a lumen when in a radially-expanded state, and activating includes activating the heating device to increase an average temperature within the lumen by no more than 2 degrees C.

For some applications, activating includes activating the heating device to apply the thermal energy using predetermined electrical parameters.

For some applications, the aneurysm is selected from the group consisting of: an abdominal aortic aneurysm and an iliac artery aneurysm, and activating includes activating the heating device to apply the thermal energy sufficient to coagulate the blood flowing into the selected aneurysm.

For some applications, the stent-graft, when in a radially-expanded state, is shaped so as to define at least one lumen having an upstream end, and activating includes activating the heating device to apply the thermal energy in a vicinity of the upstream end.

For some applications, the heating device is attached to the stent-graft, and activating includes activating the heating device that is attached to the stent-graft. For some applications, the heating device includes one or more heating elements that are attached externally around a portion of the stent-graft, and activating includes activating the heating device to drive the heating elements to apply the thermal energy. For some applications, the heating device includes one or more heating elements that are positioned within the stent-graft, and activating includes activating the heating device to drive the heating elements to apply the thermal energy. For some applications, the heating device is incorporated into the stent-graft, and activating includes activating the heating device that is incorporated into the stent-graft.

For some applications, activating includes activating the heating device to apply the thermal energy generally continuously. For some applications, activating includes activating the heating device to apply the thermal energy periodically. For some applications, activating includes activating the heating device to apply the thermal energy intermittently.

For some applications, activating includes setting one or more electrical parameters of the heating device to coagulate the blood flowing into the aneurysm, the parameters selected from the group consisting of: timing of the application of the thermal energy, and amplitude of the thermal energy.

For some applications, activating the heating device includes wirelessly transmitting energy to the heating device from an extracorporeal location. For some applications, activating the heating device includes inductively driving a current through a heating coil of the heating device to generate the thermal heat.

For some applications, activating includes activating the heating device to apply the thermal energy such that an average energy consumption rate over all five-second periods of heating does not exceed 5 W.

For some applications, activating includes activating the heating device to monitor at least one blood flow parameter, and to apply the thermal energy responsively to the at least one monitored blood flow parameter. For some applications, the stent-graft is shaped so as to define at least one lumen when in a radially-expanded state, and the at least one blood flow parameter is selected from the group consisting of: a blood flow parameter of blood flowing within the lumen, and a blood flow parameter of blood external to the lumen. For some applications, activating includes activating the heating device to set at least one heating parameter responsively to the at least one monitored blood flow parameter, so as to selectively coagulate the blood flowing into the aneurysm without causing substantial coagulation of the blood flowing within the lumen.

For some applications, activating includes activating the heating device to monitor at least one temperature, and to apply the thermal energy responsively to the at least one monitored temperature. For some applications, the stent-graft is shaped so as to define at least one lumen when in a radially-expanded state, and the at least one temperature is selected from the group consisting of: a temperature of blood flowing within the lumen, and a temperature of blood external to the lumen. For some applications, activating includes activating the heating device to set at least one heating parameter responsively to the at least one monitored temperature, so as to selectively coagulate the blood flowing into the aneurysm without causing substantial coagulation of the blood flowing within the lumen.

For some applications, the method further includes monitoring at least one blood flow parameter from an extracorporeal location, and activating includes activating the heating device to apply the thermal energy responsively to the at least one monitored blood flow parameter. For some applications, the stent-graft is shaped so as to define at least one lumen when in a radially-expanded state, and the at least one blood flow parameter is selected from the group consisting of: a blood flow parameter of blood flowing within the lumen, and a blood flow parameter of blood external to the lumen. For some applications, activating includes activating the heating device to set at least one heating parameter responsively to the at least one monitored blood flow parameter, so as to selectively coagulate the blood flowing into the aneurysm without causing substantial coagulation of the blood flowing within the lumen. For some applications, monitoring includes performing blood-flow imaging.

There is additionally provided, in accordance with an application of the present invention, apparatus including:

an endovascular stent-graft, configured to be implanted in at least one blood vessel in a vicinity of an aneurysm; and a current application device, which is coupled to the stent-graft, and which is configured to apply, to a region external to the stent-graft, an electrical current sufficient to coagulate blood flowing into the aneurysm.

For some applications, the current application device is configured to set a level of the electrical current to be insufficient to cause tissue ablation of an adventitial layer of the aneurysm.

For some applications, the current application device is configured to configure the electrical current to heat the blood.

For some applications, the current application device is configured to configure the electrical current to heat the blood by electrophoresis.

For some applications, the region surrounds at least 180 degrees of a circumference of the stent-graft, and the current application device is configured to apply the electrical current to the region.

For some applications, the current application device includes at least one sensor, and one or more electrodes. For some applications, the sensor includes a temperature sensor, and the current application device further includes circuitry which is configured to monitor at least one temperature using the temperature sensor, and to drive the one or more electrodes to apply the electrical current responsively to the at least one monitored temperature. For some applications, the sensor includes a blood flow sensor, and the current application device further includes circuitry which is configured to monitor at least one blood flow parameter using the blood flow sensor, and to drive the one or more electrodes to apply the electrical current responsively to the at least one monitored blood flow parameter.

There is yet additionally provided, in accordance with an application of the present invention, a method including:

identifying that a patient has an aneurysm; and in response to the identifying, activating an implanted current application device to apply, to a region external to an endovascular stent-graft implanted in at least one blood vessel of the patient, which region is upstream of the aneurysm, an electrical current sufficient to coagulate blood flowing into the aneurysm.

For some applications, identifying includes ascertaining that the patient is at risk of suffering from a type I endoleak, and activating includes activating the current application device to apply the thermal energy to coagulate the blood so as to reduce or prevent the type I endoleak. Alternatively or additionally, for some applications, identifying includes ascertaining that the patient suffers from a type I endoleak, and activating includes activating the current application device to apply the thermal energy to coagulate the blood so as to treat the type I endoleak.

There is also provided, in accordance with an application of the present invention, a method including:

implanting, in at least one blood vessel of a patient in a vicinity of an aneurysm, an endovascular stent-graft and a current application device coupled thereto; and activating the current application device to apply, to a region external to the stent-graft upstream of the aneurysm, an electrical current sufficient to coagulate blood flowing into the aneurysm.

For some applications, activating includes activating the current application device to set a level of the electrical current to be insufficient to cause tissue ablation of an adventitial layer of the aneurysm.

For some applications, activating includes activating the current application device to configure the electrical current to heat the blood.

For some applications, activating includes activating the current application device to configure the electrical current to heat the blood by electrophoresis.

For some applications, the aneurysm is selected from the group consisting of: an abdominal aortic aneurysm and an iliac artery aneurysm, and activating includes activating the current application device to apply the electrical current sufficient to coagulate the blood flowing into the selected aneurysm.

For some applications, activating includes activating the current application device to monitor at least one blood flow parameter, and to apply the electrical current responsively to the at least one monitored blood flow parameter.

For some applications, activating includes activating the current application device to monitor at least one temperature, and to apply the electrical current responsively to the at least one monitored temperature.

The present invention will be more fully understood from the following detailed description of embodiments thereof, taken together with the drawings, in which:

BRIEF DESCRIPTION OF THE DRAWINGS

FIGS. 1 and 2 are schematic illustrations of an endovascular stent-graft system, in accordance with respective applications of the present invention;

FIGS. 4 and 5 are schematic block diagrams of the endovascular stent-graft system of FIGS. 1, 2, and/or 3, in accordance with respective applications of the present invention;

FIG. 6 is a schematic illustration of an exemplary deployment of the endovascular stent-graft system of FIGS. 1, 2, and/or 3 in an aneurysmatic abdominal aorta, in accordance with an application of the present invention; and FIG. 7 is a schematic illustration of another configuration of the endovascular stent-graft system of FIGS. 1, 2, and/or 3, in accordance with an application of the present invention.

DETAILED DESCRIPTION OF APPLICATIONS

Figure 3:
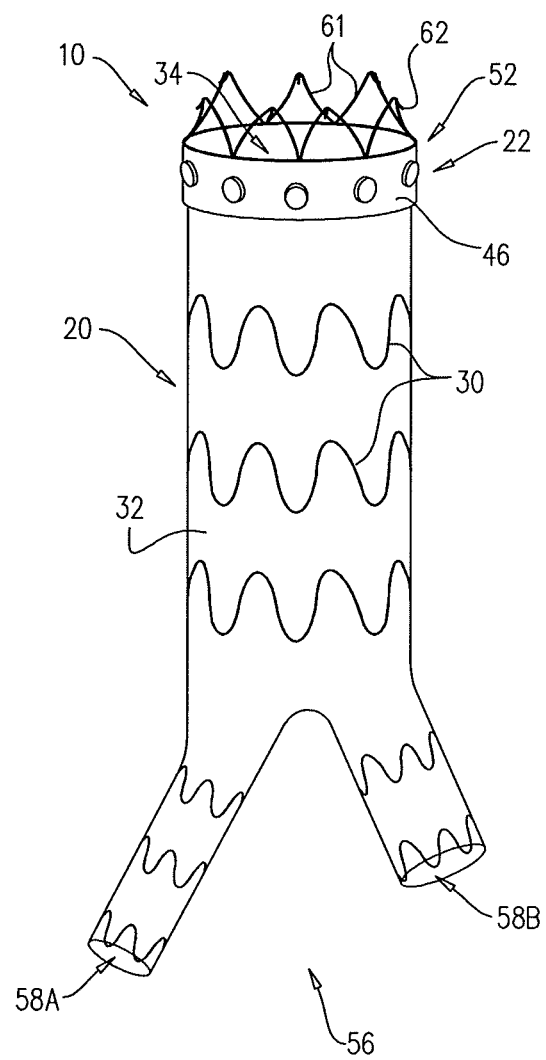
FIG. 3 is a schematic illustration of a bifurcated configuration of the stent-graft system of FIGS. 1 and/or 2, in accordance with an application of the present invention.

FIGS. 1 and 2 are schematic illustrations of an endovascular stent-graft system 10, in accordance with respective applications of the present invention. Endovascular stent-graft system 10 is typically configured to be implanted in at least one blood vessel (such as an artery) in a vicinity of an aneurysm, such as described hereinbelow with reference to FIG. 6. Endovascular stent-graft system 10 comprises an endovascular stent-graft 20 and, for some applications, a heating device 22, which is coupled to stent-graft 20. Heating device 22 is configured to apply, to a region 24 external to stent-graft 20, thermal energy sufficient to coagulate blood flowing into the aneurysm.

Stent-graft 20 typically comprises a stent 30 (which serves as a structural member) and a graft 32, which is shaped as a fluid flow guide. Typically, when stent-graft 20 is in a radially-expanded state, the stent and the graft are generally tubular. Stent 30 typically comprises a plurality of structural stent elements, such as struts. For some applications, at least some of (e.g., all of) the structural stent elements are interconnected, while for other applications, at least a portion of (e.g., all of) the structural stent elements are not interconnected. For some applications, stent 30 comprises a metal, such as stainless steel, a cobalt chromium alloy, a platinum/tungsten alloy, and a nickel-titanium alloy. Alternatively or additionally, the stent comprises a self-expanding elastic material. Alternatively or additionally, the stent comprises a superelastic alloy, such as Nitinol. For some applications, stent 30 comprises a wire stent, while for other applications, stent 30 comprises a ribbon stent. For some applications, stent 30 is formed from tubing.

Graft 32 comprises at least one biologically-compatible substantially fluid-impervious flexible sheet, which is coupled to stent 30, either outside or within the stent, such as by stitching, and covers either an external or an internal surface of at least a portion of the stent. The flexible sheet may comprise, for example, a polymer (e.g., a fluoropolymer, such as polytetrafluoroethylene, or a polyester, such as polyethylene terephthalate (PET)), natural tissue (e.g., saphenous vein or collagen), or a combination thereof.

For some applications, stent-graft 20 is configured to initially be positioned in a delivery catheter in a radially-compressed state, and to assume a radially-expanded state upon being deployed from the delivery catheter. When in the radially-expanded state, stent-graft 20 is shaped so as to define a lumen 34. FIGS. 1-3 and 6-7 show the stent-graft in the radially-expanded state. For some applications, the stent-graft is heat-set to assume the radially-expanded state. Typically, heating device 22 is also configured to assume a radially-compressed state when positioned in the delivery catheter with the stent-graft, and to expand as the stent-graft expands upon being released from the delivery catheter.

Typically, region 24 (to which heating device 22 applies the thermal energy) surrounds at least 180 degrees (such as 360 degrees) of a circumference 40 of stent-graft 20. (The at least 180 degrees are not necessarily contiguous, and may include a plurality of distinct circumferential portions.)

For some applications, heating device 22 comprises one or more heating elements 42 that are coupled to stent-graft 20, and span at least 300 degrees (such as 360 degrees) of circumference 40 of lumen 34. (The at least 300 degrees are not necessarily contiguous, and may include a plurality of distinct circumferential portions.) Heating elements 42 are positioned either at locations outside lumen 34 (as shown in FIG. 1), such as around the lumen, and/or within the lumen (configuration not shown). For some applications, the one or more heating elements 42 comprise at least one heating coil 44, which may be wrapped around a portion of stent-graft 20. For example, the heating coil may be wrapped around the portion between one and 10 times, and/or the coil may have an axial length along stent-graft 20 of between 0.5 and 4 cm. For some applications, heating coil 44 is exposed to region 24, such as shown in FIG. 1, while for other applications, heating coil 44 is covered by a covering 46, such as shown in FIG. 2 (and FIGS. 3, 6, and 7, described hereinbelow).

Alternatively, for some applications, heating device 22 drives an electrical current through a portion of the structural stent elements (e.g., struts) in order to apply the thermal energy; in other words, the portion of the structural stent elements serves as heating elements 42. Optionally, this portion of the structural stent elements is configured to have a higher resistance than the other structural stent elements; for example, the portion of the structural stent elements may be coated, and/or may comprise a material (e.g., a metal) having a higher resistance than the other structural stent elements.

When stent-graft 20 is in its radially-expanded state, lumen 34 has an axial length L which, for example, may be at least 3 cm, no more than 30 cm, and/or between 3 and 30 cm. The one or more heating elements 42 collectively are positioned along a longitudinal portion 50 of lumen 34, a length of which portion is typically no more than 50% of axial length L, such as no more than 30%, no more than 20%, or no more than 10% of axial length L. For some applications, the one or more heating elements 42 are coupled to the stent-graft in a vicinity of an upstream end 52 of lumen 34. For example, all of the heating elements may be positioned within a distance of upstream end 52, measured along an axis of the lumen, which distance is no more than 60% of axial length L, such as no more than 10% of axial length L.

For some applications, the one or more heating elements 42 have respective surfaces that apply the thermal energy. A combined total area of the surfaces may be at least 1%, no more than 10%, and/or between 1% and 10% of an average cross-sectional area of lumen 34 along longitudinal portion 50.

For some applications, heating device 22 comprises one or more sensors 60, such as exactly one sensor, or at least four sensors. One or more of the sensors may be coupled to an external surface of lumen 34, and/or one or more of the sensors may be positioned within the lumen. Typically, the one or more sensors are positioned in a vicinity of upstream end 52 of lumen 34, such as within 1 cm of the upstream end. For some applications in which heating device 22 comprises a plurality of sensors 60, the sensors are distributed around circumference 40 of stent-graft 20, for example as shown in FIG. 2.

For some applications, at least one of sensors 60 comprises a temperature sensor. Alternatively or additionally, for some applications, at least one of sensors 60 comprises a blood flow sensor. For example, the blood flow sensor may comprise one or more ultrasonic transducers, as known in the blood flow measurement art.

For some applications, heating device 22 is incorporated into stent-graft 20 during manufacture of the stent-graft. For other applications, the heating device is attached to the stent-graft after manufacture of the stent-graft, such as by a healthcare worker prior to implantation of the stent-graft, or by a distributor of the stent-graft. For some applications, heating device 22 is provided as a separate unit, and attached to a stent-graft not specially pre-configured for use with the heating device.

Reference is now made to FIG. 3, which is a schematic illustration of a bifurcated configuration of stent-graft system 10, in accordance with an application of the present invention. Other than as described below, this configuration is generally similar to the configurations described hereinabove with reference to FIGS. 1 and 2. In this configuration, lumen 34 is a main lumen 54, and stent-graft 20 is shaped so as to define a bifurcated downstream end 56, which defines first and second generally tubular downstream lumens 58A and 58B that are in fluid communication with main lumen 54. As mentioned above, for some applications, the one or more heating elements 42 may be coupled to stent-graft 20 in a vicinity of upstream end 52 of the main lumen.

For some applications, stent-graft 20 is shaped so as to define at least one flared end. For example, upstream end 52 may be flared, as shown in FIGS. 3 and 6. For some applications, an upstream-most first portion of the structural stent elements of stent 30 are shaped so as to define a plurality of anchoring elements 61 that extend radially outwardly, and, optionally, upstream, when the stent-graft assumes the radially-expanded state, as shown in FIGS. 3 and 6. The anchoring elements anchor the stent-graft to the vascular wall, helping prevent dislodgement. Optionally, one or more of anchoring elements 61 are shaped so as to define respective barbs 62. (As used in the present application, including in the claims, a "barb" means an element having at least one free sharp end, which is sharp enough to enter the aortic wall. The element does not necessarily define a sharp projection extending backward from the sharp end for preventing easy extraction.)

Reference is now made to FIGS. 4 and 5, which are schematic block diagrams of endovascular stent-graft system 10, in accordance with respective applications of the present invention. In the configurations shown in both FIGS. 4 and 5, heating device 22 comprises circuitry 70, which is configured to drive heating elements 42 to apply the thermal energy, as described hereinabove with reference to FIGS. 1 and 2. Circuitry 70 may comprise, for example, one or more processors and/or memory, as is known in the art.

For some applications, heating device 22 is configured for wireless control from an extracorporeal location. For some of these applications, such as in the configurations shown in both FIGS. 4 and 5, heating device 22 comprises a communication unit 72, which is configured to communicate with a wireless remote control unit 74 of an extracorporeal control unit 76. The wireless remote control unit enables control of heating device 22 from an extracorporeal location, for example as described hereinbelow.

For some applications, as in the configuration shown in FIG. 4, heating device 22 further comprises a power supply 77, which may comprise, for example, one or more batteries or capacitors, which are optionally rechargeable. Alternatively or additionally, for some applications, as in the configuration shown in FIG. 5, heating device 22 further comprises a power receiver and storage unit 78, which is configured to wirelessly receive energy from an extracorporeal energizer 80, either of extracorporeal control unit 76, or of a separate unit. Power receiver and storage unit 78 typically comprises one or more wire coils 82 for wirelessly receiving energy transmitted by extracorporeal energizer 80. For example, the one or more coils may be wrapped around a portion lumen 34, such as shown in FIG. 1.

Further alternatively, for some applications, extracorporeal control unit 76 is configured to wirelessly transmit energy directly to the one or more heating elements 42, such as for applications in which the one or more heating elements comprise the at least one heating coil 44. For example, the extracorporeal control unit may be configured to inductively drive current through the heating coil to generate the thermal heat, or the extracorporeal control unit may be configured to apply an alternating magnetic field to the heating coil, which may comprise a ferromagnetic material. For these applications, power supply 77, power receiver and storage unit 78, and/or circuitry 70 are not necessarily provided. Optionally, a portion of the structural elements of stent 30 serve as the coil, as described hereinabove.

For some applications, circuitry 70 is configured to drive the one or more heating elements 42 to apply the thermal energy by driving a current through the heating elements. For some applications, circuitry 70 is configured to set one or more electrical parameters of the current to coagulate the blood flowing into the aneurysm, the parameters selected from the group consisting of: timing of the application of the thermal energy, and amplitude of the thermal energy.

For some applications, circuitry 70 is configured to drive the one or more heating elements 42 to apply the thermal energy such that an average energy consumption rate over all five-second periods of heating does not exceed 5 W, such as does not exceed 2 W, and/or is at least 0.1 W. For some applications, circuitry 70 is configured to drive the heating elements 42 to apply the thermal energy generally continuously. Alternatively, for some applications, circuitry 70 is configured to drive the heating elements 42 to apply the thermal energy generally periodically, such as a number of minutes per day (e.g., at least one, no more than five, or between one and five minutes per day), or a number of minutes per week. Further alternatively, for some applications, circuitry 70 is configured to drive the heating elements 42 to apply the thermal energy generally intermittently. Still further alternatively, for some applications, circuitry 70 is configured to drive the heating elements 42 to apply the thermal energy a predetermined number of times, such as exactly once (e.g., soon after implantation). For some applications, heating device 22 is configured to apply the thermal energy using predetermined electrical parameters. For some applications, heating device 22 is configured to apply the thermal energy such that an average energy consumption rate over all five-second periods of heating does not exceed 5 W, such as does not exceed 2 W, and/or is at least 0.1 W.

For some applications, at least one of sensors 60 comprises a temperature sensor, and circuitry 70 is configured to monitor at least one temperature using the temperature sensor, and to drive the one or more heating elements 42 to apply the thermal energy responsively to the at least one monitored temperature. Heating device 22 thus applies the thermal energy in a closed loop, in order to achieve a desired, typically predetermined, temperature, using the monitored temperature as the sensed feedback variable.

For some applications, the temperature sensor is configured (e.g., positioned) to measure the temperature of blood flowing within lumen 34, while for other applications, the temperature sensor is configured (e.g., positioned) to measure the temperature of blood external to lumen 34 (such as in region 24). Alternatively, a plurality of temperature sensors are provided, and one or more are configured to measure the temperature of the blood flowing within the lumen, and one or more are configured to measure the temperature of the blood external to the lumen. For some applications, circuitry 70 is configured to maintain the temperature of the blood external to the lumen at between a minimum temperature (e.g., between 39 and 41 degrees C., such as 39 degrees C.) and a maximum temperature (e.g., between 41 and 45 degrees C., such as 44 degrees C.). For some applications, circuitry 70 is configured to set at least one heating parameter responsively to the at least one temperature, so as to selectively coagulate the blood flowing into the aneurysm without causing substantial coagulation of the blood flowing within the lumen.

For some applications, at least one of sensors 60 comprises a blood flow sensor, and circuitry 70 is configured to monitor at least one blood flow parameter (e.g., velocity or pressure) using the blood flow sensor, and to drive the one or more heating elements 42 to apply the thermal energy responsively to the at least one monitored blood flow sensor. Heating device 22 thus applies the thermal energy in a closed loop, in order to achieve a desired, typically predetermined, blood flow parameter (such as velocity or pressure), using the monitored blood flow parameter as the sensed feedback variable.

For some applications, the blood flow sensor is configured (e.g., positioned) to measure the blood flow parameter of blood flowing within lumen 34, while for other applications, the blood flow sensor is configured (e.g., positioned) to measure the blood flow parameter of blood external to lumen 34 (such as in region 24). Alternatively, a plurality of blood flow sensors are provided, and one or more are configured to measure the blood flow parameter of the blood flowing within the lumen, and one or more are configured to measure the blood flow parameter of the blood external to the lumen. For some applications, circuitry 70 is configured to set at least one heating parameter responsively to the at least one blood flow parameter, so as to selectively coagulate the blood flowing into the aneurysm without causing substantial coagulation of the blood flowing within the lumen.

For some applications, heating device 22 is configured to set a level of the thermal energy to increase an average temperature in region 24 by between 3 and 7 degrees C. For some applications, heating device 22 is configured to set a level of the thermal energy to increase an average temperature in region 24 by no more than 6 degrees C. For some applications, heating device 22 is configured to set a level of the thermal energy to increase an average temperature in region 24 to between a minimum temperature (e.g., between 39 and 41 degrees C., such as 39 degrees C.) and a maximum temperature (e.g., between 41 and 45 degrees C., such as 44 degrees C.). For some applications, heating device 22 is configured to increase an average temperature within lumen 34 by no more than 2 degrees C.

Reference is made to FIG. 6, which is a schematic illustration of an exemplary deployment of endovascular stent-graft system 10 in an aneurysmatic abdominal aorta 100, in accordance with an application of the present invention. Stent-graft 20 is shown in its radially-expanded state, deployed in aneurysmatic abdominal aorta 100 to bypass an abdominal aneurysm 102. The stent-graft extends from a sub-renal neck 103 of the aneurysm to iliac arteries 104, with branching lumens 58A and 58B positioned in respective ones of the iliac arteries. Heating device 22 is configured to apply, to region 24 external to stent-graft 20, thermal energy sufficient to coagulate blood flowing into aneurysm 102. Although system 10 is shown implanted in abdominal aorta 100, this is by way of example and not limitation; the system may alternatively be deployed in other aneurysmatic blood vessels, such as an aneurysmatic iliac artery.

For some applications, heating device 22 is configured to set a level of the thermal energy to be insufficient to cause tissue ablation, such as tissue ablation of an adventitial layer of aneurysm 102.

Typically, stent-graft 20 and heating device 22 are configured to be entirely implanted in at least one blood vessel, such that no portion of either of the stent-graft or the heating device extends outside of the at least one blood vessel. Typically, implanting the stent-graft and the heating device comprises designating the stent-graft and the heating device to remain implanted in the at least one blood vessel for at least one year.

For some applications, a method for using stent-graft system 10 comprises identifying that a patient has an aneurysm that has been treated with, or is planned to be treated be treated with endovascular stent with, endovascular stent-graft 20, and activating heating device 22 to apply, to region 24 external to stent-graft 20 upstream of the aneurysm, thermal energy sufficient to coagulate blood flowing into the aneurysm. For some applications, a method for using stent-graft system 10 comprises implanting stent-graft 20 and heating device 22 in at least one blood vessel of the patient, and activating the heating device to apply the thermal energy to region 24. Techniques for identifying that a patient has an aneurysm are well known in the art, and are thus not described herein.

For some applications, identifying comprises ascertaining that the patient is at risk of suffering from a type I endoleak, and activating comprises activating heating device 22 to apply the thermal energy to coagulate the blood so as to reduce or prevent the type I endoleak. Alternatively, identifying comprises ascertaining that the patient suffers from a type I endoleak, and activating comprises activating the heating device to apply the thermal energy to coagulate the blood so as to treat the type I endoleak.

For some applications, at least one blood flow parameter is monitored from an extracorporeal location (such as by performing blood-flow imaging), and heating device 22 is activated to apply the thermal energy responsively to the at least one monitored blood flow parameter, such as by sending a control signal from extracorporeal control unit 76. For example, the at least one blood flow parameter may be a blood flow parameter of blood flowing within lumen 34, and/or a blood flow parameter of blood external to the lumen (such as in region 24). For some applications, heating device 22 may be activated to set at least one heating parameter responsively to the at least one monitored blood flow parameter, so as to selectively coagulate the blood flowing into the aneurysm without causing substantial coagulation of the blood flowing within the lumen.

For some applications, stent-graft 20 and heating device 22 are transvascularly introduced into the at least one blood vessel. Typically, the stent-graft and the heating device are transvascularly introduced while the stent-graft and the heating device are positioned in a delivery catheter in respective radially-compressed states. The stent-graft and the heating device are deployed from the delivery catheter in the at least one blood vessel, so that the stent-graft and the heating element assume respective radially-expanded states.

Reference is now made to FIG. 7, which is a schematic illustration of another configuration of endovascular stent-graft system 10, in accordance with an application of the present invention. This configuration of the system is generally similar to the configurations described hereinabove with reference to FIGS. 1-6, any may incorporate any of the features of the applications described with reference to these figures, as appropriate, *mutatis mutandis*. However, unlike in the applications described with reference to FIGS. 1-6, in the configuration of FIG. 7 stent-graft system 10 comprises a current application device 130, rather than heating device 22. Current application device 130 typically comprises a plurality of electrodes 132, and circuitry 70 is configured to drive the electrodes to apply, to region 24 external to the stent-graft, an electrical current sufficient to coagulate blood flowing into the aneurysm. For some applications, current application device 130 is configured to configure the electrical current to heat the blood by electrophoresis. Typically, the current application device is configured to set a level of the electrical current to be insufficient to cause tissue ablation, such as tissue ablation of an adventitial layer of the aneurysm. For example, the current application device may be configured to maintain or achieve the temperatures and/or temperature changes of the blood external to the lumen and/or region 24 described hereinabove with reference to FIGS. 4 and 5. Alternatively, for some applications, system 10 comprises both current application device 130 and heating device 22.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally elliptical but not circular, or circular. As used in the present application, including in the claims, "suffering" means having a disease or condition.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529, 936 in the national stage thereof, which published as US Patent Application Publication 2010/0063575

U.S. application Ser. No. 12/529,936, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCTAB2010/052861, filed Jun. 23, 2010, which published as PCT Publication WO 2010/150208 to Shalev et al.

PCT Application PCT/IL2010/000564, filed Jul. 14, 2010, which published as PCT Publication WO 2011/007354 to Benary et al.

PCT Application PCT/IL2010/000917, filed Nov. 4, 2010, which published as PCT Publication WO 2011/055364

PCT Application PCT/IL2010/000999, filed Nov. 30, 2010, entitled, "Multi-component stent-graft system for implantation in a blood vessel with multiple branches," which published as PCT Publication WO 2011/064782

PCT Application PCT/IL2010/001018, filed Dec. 2, 2010, entitled, "Endovascular fenestrated stent-grafting," which published as PCT Publication WO 2011/067764

PCT Application PCT/IL2010/001037, filed Dec. 8, 2010, entitled, "Endovascular stent-graft system with fenestrated and crossing stent-grafts," which published as PCT Publication WO 2011/070576

PCT Application PCT/IL2010/001087, filed Dec. 27, 2010, entitled, "Endovascular flow direction indicator," which published as PCT Publication WO 2011/080738

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
an endovascular stent-graft, configured to be implanted in at least one blood vessel in a vicinity of an aneurysm, and shaped so as to define a lumen having an axial length when in a radially-expanded state; and
a heating device, which is coupled to the stent-graft, which is (i) is incorporated into the stent-graft during manufacture of the stent-graft, (ii) is configured to assume a radially-compressed state with the stent-graft, (iii) is configured to apply, to a region external to the stent-graft, thermal energy sufficient to coagulate blood flowing into the aneurysm, and which (iv) comprises (a) one or more heating elements that collectively are positioned along no more than 20% of the axial length of the lumen, and (b) at least one sensor that is coupled to an external surface of the lumen.

2. The apparatus according to claim 1, wherein the heating device is configured to set a level of the thermal energy to increase an average temperature in the region by between 3 and 7 degrees C.

3. The apparatus according to claim 1, wherein the heating device is configured to increase an average temperature within the lumen by no more than 2 degrees C.

4. The apparatus according to claim 1, wherein the one or more heating elements have respective surfaces that apply the thermal energy, wherein the heating elements are collectively are positioned along a longitudinal portion of the lumen, and wherein a combined total area of the surfaces is between 1% and 10% of an average cross-sectional area of the lumen along the longitudinal portion.

5. The apparatus according to claim 1, wherein the heating device comprises circuitry that is configured to drive the one or more heating elements to apply the thermal energy such that an average energy consumption rate over all five-second periods of heating does not exceed 5 W.

6. The apparatus according to claim 1, wherein the heating device is configured to apply the thermal energy at a maximum energy consumption rate of between 0.5 and 2 W.

7. Apparatus comprising:
an endovascular stent-graft, configured to be implanted in at least one blood vessel in a vicinity of an aneurysm, and shaped so as to define a lumen having an axial length when in a radially-expanded state; and
a heating device, which is coupled to the stent-graft, which is (i) is incorporated into the stent-graft during manufacture of the stent-graft, (ii) is configured to assume a radially-compressed state with the stent-graft, (iii) is configured to apply, to a region external to the stent-graft, thermal energy sufficient to coagulate blood flowing into the aneurysm, and which (iv) comprises (a) one or more heating elements that collectively are positioned along no more than 20% of the axial length of the lumen, and (b) a temperature sensor, and circuitry which is configured to monitor at least a temperature of blood external to the lumen using the temperature sensor, and to drive the one or more heating elements to apply the thermal energy responsively to the at least one monitored temperature.

8. The apparatus according to claim 7, wherein the circuitry is configured to maintain the temperature of the blood external to the lumen at between a minimum and a maximum temperature, the minimum temperature between 39 and 41 degrees C., and the maximum temperature between 41 and 45 degrees C.

9. Apparatus comprising:
an endovascular stent-graft, configured to be implanted in at least one blood vessel in a vicinity of an aneurysm, and shaped so as to define a lumen having an axial length when in a radially-expanded state; and
a heating device, which is coupled to the stent-graft, which is (i) is incorporated into the stent-graft during manufacture of the stent-graft, (ii) is configured to assume a radially-compressed state with the stent-graft, (iii) is configured to apply, to a region external to the stent-graft, thermal energy sufficient to coagulate blood flowing into the aneurysm, and which (iv) comprises (a) one or more heating elements that collectively are positioned along no more than 20% of the axial length of the lumen, and (b) a temperature sensor and circuitry which is configured to:
monitor, using the temperature sensor, at least one temperature selected from the group consisting of: a temperature of blood flowing within the lumen, and a temperature of blood external to the lumen,
drive the one or more heating elements to apply the thermal energy responsively to the at least one monitored temperature, and
set at least one heating parameter responsively to the at least one temperature, so as to selectively coagulate the blood flowing into the aneurysm without causing substantial coagulation of the blood flowing within the lumen.

10. Apparatus comprising:
an endovascular stent-graft, configured to be implanted in at least one blood vessel in a vicinity of an aneurysm, and shaped so as to define a lumen having an axial length when in a radially-expanded state; and
a heating device, which is coupled to the stent-graft, which is (i) is incorporated into the stent-graft during manufacture of the stent-graft, (ii) is configured to assume a radially-compressed state with the stent-graft, (iii) which is configured to apply, to a region external to the stent-graft, thermal energy sufficient to coagulate blood flowing into the aneurysm, and which (iv) comprises (a) one or more heating elements that collectively are positioned along no more than 20% of the axial length of the lumen, and (b) a blood flow sensor, and circuitry which is configured to monitor at least one blood flow parameter of blood external to the lumen using the blood flow sensor, and to drive the one or more heating elements to apply the thermal energy responsively to the at least one monitored blood flow parameter.

11. Apparatus comprising:
an endovascular stent-graft, configured to be implanted in at least one blood vessel in a vicinity of an aneurysm, and shaped so as to define a lumen having an axial length when in a radially-expanded state; and
a heating device, which is coupled to the stent-graft, which is (i) is incorporated into the stent-graft during manufacture of the stent-graft, (ii) is configured to assume a radially-compressed state with the stent-graft, (iii) which is configured to apply, to a region external to the stent-graft, thermal energy sufficient to coagulate blood flowing into the aneurysm, and which (iv) comprises (a) one or more heating elements that collectively are positioned along no more than 20% of the axial length of the lumen, and (b) a blood flow sensor, and circuitry which is configured to:
monitor, using the blood flow sensor, at least one blood flow parameter selected from the group consisting of: a blood flow parameter of blood flowing within the lumen, and a blood flow parameter of blood external to the lumen, and
set at least one heating parameter responsively to the at least one monitored blood flow parameter, so as to selectively coagulate the blood flowing into the aneurysm without causing substantial coagulation of the blood flowing within the lumen.

12. The apparatus according to claim 7, wherein the temperature sensor is coupled to an external surface of the lumen.

13. Apparatus comprising:
an endovascular stent-graft, configured to be implanted in at least one blood vessel in a vicinity of an aneurysm, and shaped so as to define a lumen having an axial length when in a radially-expanded state; and
a heating device, which is coupled to the stent-graft, which is (i) is incorporated into the stent-graft during manufacture of the stent-graft, (ii) is configured to assume a radially-compressed state with the stent-graft, (iii) which is configured to apply, to a region external to the stent-graft, thermal energy sufficient to coagulate blood flowing into the aneurysm, and which (iv) comprises (a) one or more heating elements that collectively are positioned along no more than 20% of the axial length of the lumen, and (b) at least one sensor positioned in a vicinity of an upstream end of the lumen.

14. The apparatus according to claim 1, wherein the stent-graft comprises a stent and a graft coupled to the stent, which stent and graft are generally tubular when the stent-graft is in an radially-expanded state, and wherein the stent comprises a plurality of structural stent elements, and wherein the heating device drives an electrical current through a portion of the structural stent elements in order to apply the thermal energy.

15. The apparatus according to claim 1, wherein the heating device is configured with one or more electrical parameters that are set to coagulate the blood flowing into the aneurysm, the parameters selected from the group consisting of: timing of the application of the thermal energy, and amplitude of the thermal energy.

16. A method comprising:
identifying that a patient has an aneurysm; and
in response to the identifying, activating an implanted heating device to apply, to a region external to an endovascular stent-graft implanted in at least one blood vessel of the patient in a vicinity of the aneurysm, which region is upstream of the aneurysm, thermal energy sufficient to coagulate blood flowing into the aneurysm, wherein the endovascular stent-graft is shaped so as to define a lumen having an axial length when in a radially-expanded state, and wherein the heating device is coupled to the stent-graft, and (i) is incorporated into the stent-graft during manufacture of the stent-graft, (ii) is configured to assume a radially-compressed state with the stent-graft, and (iii) comprises (a) one or more heating elements that collectively are positioned along no more than 20% of the axial length of the lumen, and (b) at least one sensor that is coupled to an external surface of the lumen.

17. The method according to claim 16, wherein identifying comprises ascertaining that the patient is at risk of suffering from a type I endoleak, and wherein activating comprises activating the heating device to apply the thermal energy to coagulate the blood so as to reduce or prevent the type I endoleak.

18. The method according to claim 16, wherein identifying comprises ascertaining that the patient suffers from a type I endoleak, and wherein activating comprises activating the heating device to apply the thermal energy to coagulate the blood so as to treat the type I endoleak.

19. A method comprising:
implanting, in at least one blood vessel of a patient in a vicinity of an aneurysm, (a) an endovascular stent-graft, which is shaped so as to define a lumen having an axial length when in a radially-expanded state, (b) and a heating device that is coupled to the stent-graft and (i) is incorporated into the stent-graft during manufacture of the stent-graft, (ii) is configured to assume a radially-compressed state with the stent-graft, and (iii) comprises (i) one or more heating elements that collectively are positioned along no more than 20% of the axial length of the lumen, and (ii) at least one sensor that is coupled to an external surface of the lumen; and
activating the heating device to apply, to a region external to the stent-graft and upstream of the aneurysm, thermal energy sufficient to coagulate blood flowing into the aneurysm.

20. The method according to claim 19, wherein activating comprises:
ascertaining that the patient has is at risk of suffering from a type I endoleak; and
activating the heating device to apply the thermal energy to coagulate the blood so as to reduce or prevent the type I endoleak.

21. The method according to claim 19, wherein activating comprises:
ascertaining that the patient suffers from a type I endoleak; and
activating the heating device to apply the thermal energy to coagulate the blood so as to treat the type I endoleak.

22. The method according to claim 16, wherein activating comprises activating the heating device to apply the thermal energy at a level that selectively coagulates the blood flowing into the aneurysm without causing substantial coagulation of blood flowing within the lumen.

23. The method according to claim 16, wherein activating comprises activating the heating device to increase an average temperature within the lumen by no more than 2 degrees C.

24. The method according to claim 16, wherein the aneurysm is selected from the group consisting of: an abdominal aortic aneurysm and an iliac artery aneurysm, and wherein activating comprises activating the heating device to apply the thermal energy sufficient to coagulate the blood flowing into the selected aneurysm.

25. The method according to claim 16, activating comprises activating the heating device to monitor at least one blood flow parameter of blood external to the lumen, and to apply the thermal energy responsively to the at least one monitored blood flow parameter.

26. The method according to claim 16, wherein activating comprises:
activating the heating device to monitor at least one blood flow parameter selected from the group consisting of: a blood flow parameter of blood flowing within the lumen, and a blood flow parameter of blood external to the lumen; and
activating the heating device to set at least one heating parameter responsively to the at least one monitored blood flow parameter, so as to selectively coagulate the blood flowing into the aneurysm without causing substantial coagulation of the blood flowing within the lumen.

27. The method according to claim 16, wherein activating comprises activating the heating device to monitor at least a temperature of blood external to the lumen, and to apply the thermal energy responsively to the at least one monitored temperature.

28. The method according to claim 16, wherein activating comprises:
activating the heating device to monitor at least one temperature selected from the group consisting of: a temperature of blood flowing within the lumen, and a temperature of blood external to the lumen; and
activating the heating device to set at least one heating parameter responsively to the at least one monitored temperature, so as to selectively coagulate the blood flowing into the aneurysm without causing substantial coagulation of the blood flowing within the lumen.

29. The method according to claim 16, wherein the method further comprises monitoring at least one blood flow parameter from an extracorporeal location, and wherein activating comprises activating the heating device to apply the thermal energy responsively to the at least one monitored blood flow parameter.

30. The apparatus according to claim 1, wherein the one or more heating elements are collectively positioned along no more than 10% of the axial length of the lumen.

31. The apparatus according to claim 30, wherein all of the heating elements are positioned within a distance of an upstream end of the lumen, measured along an axis of the lumen, which distance is no more than 10% of the axial length of the lumen.

32. The method according to claim 16, wherein all of the heating elements are positioned within a distance of an upstream end of the lumen, measured along an axis of the lumen, which distance is no more than 10% of the axial length of the lumen, and wherein activating an implanted heating device comprises activating the heating elements to apply the thermal energy to the region upstream of the aneurysm.

33. The method according to claim 19, wherein the stent-graft is shaped so as to define at least one lumen when in a radially-expanded state, and wherein activating comprises activating the heating device to apply the thermal energy at a level that selectively coagulates the blood flowing into the aneurysm without causing substantial coagulation of blood flowing within the lumen.

34. The method according to claim 19, wherein activating comprises activating the heating device to increase an average temperature within the lumen by no more than 2 degrees C.

35. The method according to claim 19, wherein the aneurysm is selected from the group consisting of: an abdominal aortic aneurysm and an iliac artery aneurysm, and wherein activating comprises activating the heating device to apply the thermal energy sufficient to coagulate the blood flowing into the selected aneurysm.

36. The method according to claim 19, wherein activating comprises activating the heating device to monitor at least one blood flow parameter of blood external to the lumen, and to apply the thermal energy responsively to the at least one monitored blood flow parameter.

37. The method according to claim 19, wherein activating comprises:
   activating the heating device to monitor at least one blood flow parameter selected from the group consisting of: a blood flow parameter of blood flowing within the lumen, and a blood flow parameter of blood external to the lumen; and
   activating the heating device to set at least one heating parameter responsively to the at least one monitored blood flow parameter, so as to selectively coagulate the blood flowing into the aneurysm without causing substantial coagulation of the blood flowing within the lumen.

38. The method according to claim 19, wherein activating comprises activating the heating device to monitor at least a temperature of blood external to the lumen, and to apply the thermal energy responsively to the at least one monitored temperature.

39. The method according to claim 19, wherein activating comprises:
   activating the heating device to monitor at least one temperature selected from the group consisting of: a temperature of blood flowing within the lumen, and a temperature of blood external to the lumen; and
   activating the heating device to set at least one heating parameter responsively to the at least one monitored temperature, so as to selectively coagulate the blood flowing into the aneurysm without causing substantial coagulation of the blood flowing within the lumen.

40. The method according to claim 19, wherein the method further comprises monitoring at least one blood flow parameter from an extracorporeal location, and wherein activating comprises activating the heating device to apply the thermal energy responsively to the at least one monitored blood flow parameter.

41. The method according to claim 19, wherein all of the heating elements are positioned within a distance of an upstream end of the lumen, measured along an axis of the lumen, which distance is no more than 10% of the axial length of the lumen, and wherein activating an implanted heating device comprises activating the heating elements to apply the thermal energy to the region upstream of the aneurysm.

42. The method according to claim 19, wherein the one or more heating elements are collectively positioned along no more than 10% of the axial length of the lumen.

43. The method according to claim 16, wherein the one or more heating elements are collectively positioned along no more than 10% of the axial length of the lumen.

* * * * *